(12) United States Patent
Lee et al.

(10) Patent No.: US 9,457,082 B2
(45) Date of Patent: Oct. 4, 2016

(54) LIPOSOME INCLUDING COMPLEX OF HYDROPHOBIC ACTIVE INGREDIENT AND POLYPEPTIDE AND USE OF THE LIPOSOME

(71) Applicant: Samsung Electronics Co., Ltd., Suwon-si, Gyeonggi-do (KR)

(72) Inventors: Don-wook Lee, Yongin-si (KR); Ki-tae Park, Yongin-si (KR); Jung-yong Nam, Incheon (KR); Hyun-ryoung Kim, Guri-si (KR); Eun-sung Park, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 215 days.

(21) Appl. No.: 14/252,084

(22) Filed: Apr. 14, 2014

(65) Prior Publication Data
US 2015/0086611 A1   Mar. 26, 2015

(30) Foreign Application Priority Data

Sep. 26, 2013 (KR) .................. 10-2013-0114706

(51) Int. Cl.
| A61K 41/00 | (2006.01) |
| A61K 9/127 | (2006.01) |
| A61K 31/4412 | (2006.01) |
| A61K 47/40 | (2006.01) |
| A61K 47/42 | (2006.01) |
| A61N 7/02 | (2006.01) |

(52) U.S. Cl.
CPC .......... *A61K 41/0028* (2013.01); *A61K 9/1271* (2013.01); *A61K 31/4412* (2013.01); *A61K 47/40* (2013.01); *A61K 47/42* (2013.01); *A61N 7/02* (2013.01)

(58) Field of Classification Search
None
See application file for complete search history.

(56) References Cited

U.S. PATENT DOCUMENTS

| 5,683,715 | A | * | 11/1997 | Boni ...................... A61K 9/127 424/450 |
| 6,096,331 | A | | 8/2000 | Desai et al. |
| 6,200,598 | B1 | | 3/2001 | Needham |
| 6,426,086 | B1 | * | 7/2002 | Papahadjopoulos . A61K 9/1272 424/1.21 |
| 6,749,868 | B1 | * | 6/2004 | Desai ...................... A23L 1/296 424/489 |
| 7,672,704 | B2 | | 3/2010 | Viglianti et al. |
| 7,769,423 | B2 | | 8/2010 | Viglianti et al. |
| 7,901,709 | B2 | | 3/2011 | Needham |
| 2002/0150621 | A1 | | 10/2002 | Kohane et al. |
| 2009/0098212 | A1 | | 4/2009 | Fossheim et al. |
| 2009/0246127 | A1 | | 10/2009 | Hummel et al. |
| 2011/0177009 | A1 | | 7/2011 | Langereis et al. |
| 2011/0200665 | A1 | | 8/2011 | Mei et al. |
| 2012/0076862 | A1 | | 3/2012 | Desai et al. |
| 2012/0121695 | A1 | | 5/2012 | Lauten et al. |
| 2013/0072854 | A1 | | 3/2013 | Mohan et al. |

FOREIGN PATENT DOCUMENTS

| KR | 1020100094664 A | 8/2010 |
| KR | 1020130042905 A | 4/2013 |

OTHER PUBLICATIONS

Damascelli et al., Intraarterial Chemotherapy with Polyoxyethylated Castor Oil Free Paclitaxel, Incorporated in Albumin Nanoparticles (ABI-007), *Cancer*, 92(10): 2592-2602 (2001).

\* cited by examiner

*Primary Examiner* — Anand Desai
(74) *Attorney, Agent, or Firm* — Leydig, Voit & Mayer, Ltd.

(57) ABSTRACT

A liposome comprising a lipid bilayer encapsulating a complex containing a hydrophobic active ingredient and a polypeptide, a pharmaceutical composition including the liposome, and a method of delivering an active ingredient to a target site in the body of a subject.

16 Claims, 5 Drawing Sheets

LIPOSOME INCLUDING COMPLEX OF HYDROPHOBIC ACTIVE INGREDIENT AND POLYPEPTIDE AND USE OF THE LIPOSOME

RELATED APPLICATION

This application claims the benefit of Korean Patent Application No. 10-2013-0114706, filed on Sep. 26, 2013, in the Korean Intellectual Property Office, the disclosure of which is hereby incorporated by reference.

BACKGROUND

1. Field

The present invention relates to liposomes for delivering an active ingredient to a subject, and methods of delivering the active ingredient to a target site of a subject using the liposomes.

2. Description of the Related Art

Liposomes consist of at least one lipid bilayer membrane enclosing an aqueous internal compartment. Liposomes may be characterized by membrane type and by size. Small unilamellar vesicles (SUVs) may have a single membrane and have a diameter in a range of about 20 nm to about 50 nm. Large unilamellar vesicles (LUVs) may have a diameter of about 50 nm or greater. Oligolamellar large vesicles and multilamellar vesicles may have multiple, usually concentric, membrane layers and have a diameter of about 100 nm or greater. Liposomes with several non-concentric membranes, i.e., several smaller vesicles contained within in a large vesicle, are termed multivesicular vesicles.

Liposomes may be formulated to carry therapeutic agents, drugs or other active ingredients either contained within the aqueous interior space (water-soluble active ingredient) or partitioned into the lipid bilayer (water-insoluble active ingredient). In addition, a hydrophobic active ingredient such as cholesterol may be contained in a micelle. As used herein, "micelle" refers to an aggregate of surfactant molecules comprising a hydrophobic interior. A micelle comprising a hydrophobic active ingredient may be contained within the liposome aqueous interior space.

The delivery of hydrophobic drugs may be performed by emulsion, the use of co-solvents, and by micelles. In the case of the liposomes, hydrophobic drugs may be contained within the lipid bilayer of the liposome, which may affect a property of the lipid bilayer. As a result, the stability or stimulus-sensitivity of the lipid bilayer may not be retained. Additionally, hydrophobic drugs contained within the lipid bilayer of the liposome may not be efficiently released due to strong coherence between the hydrophobic drugs and the lipid bilayer.

There has been research on the use of albumin as a carrier for hydrophobic drugs since albumin has a hydrophobic pocket and accordingly may strongly bind to hydrophobic drugs. However, when albumin is used as a drug carrier, targeting with respect to diseased tissues may not be conducted. Additionally, there may be undesirable side-effects for treatments comprising albumin-bound drugs.

Therefore, a need remains for liposomes that provide the controlled release of active ingredients to act on the target site of a subject.

SUMMARY

Provided are liposomes comprising a lipid bilayer encapsulating a complex containing a hydrophobic active ingredient and a polypeptide.

Additionally, provided are pharmaceutical compositions including the liposomes to deliver the active ingredients to a subject.

Furthermore, provided are methods of delivering the hydrophobic active ingredients to a target site in the body of a subject comprising administering a pharmaceutical composition comprising the liposome to a subject, and applying a stimulus to a target site of the subject to release the complex containing the hydrophobic active ingredient and the polypeptide from the liposome.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
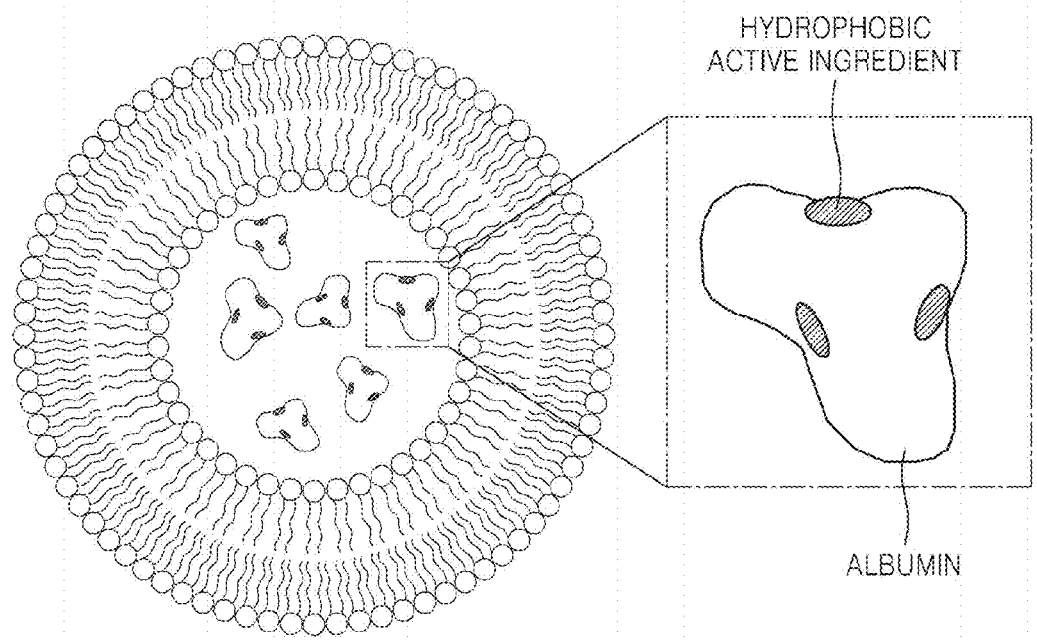
FIG. 1A is a schematic diagram illustrating a liposome including a complex containing a hydrophobic active ingredient and albumin.
Figure 1B:
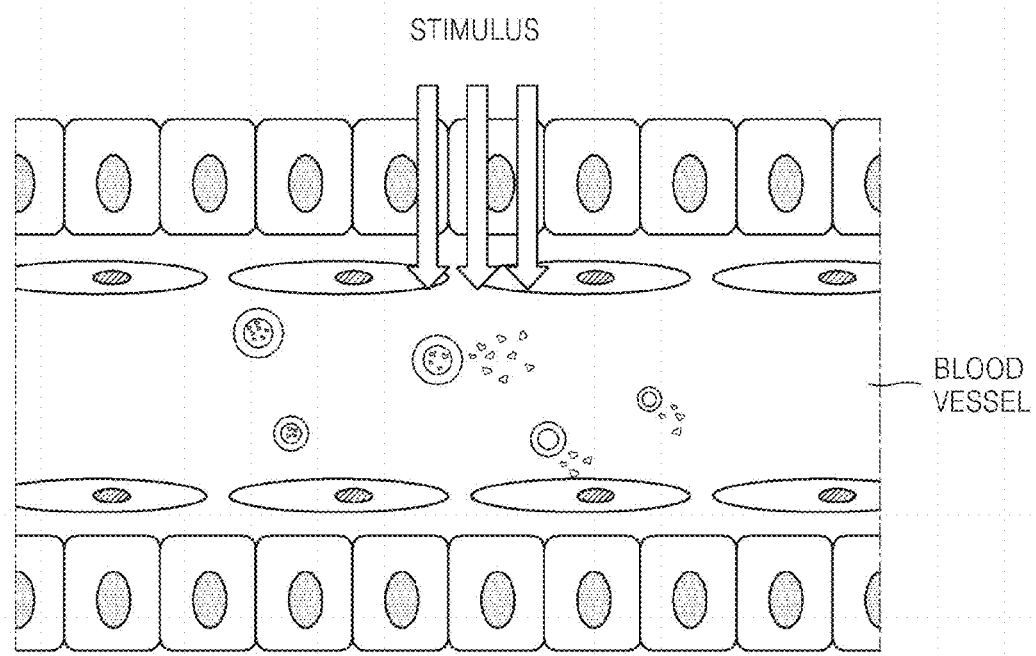
FIG. 1B is a schematic diagram illustrating a liposome releasing a complex of a hydrophobic active ingredient and albumin to a target site after exposure to an external stimulus.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

According to an aspect of the present invention, provided is a liposome comprising a complex, wherein the complex comprises a hydrophobic active ingredient and a polypeptide; and a lipid bilayer, wherein the complex is contained in an interior space of the liposome.

The term "liposome" as used herein refers to an artificially prepared vesicle composed of a lipid bilayer. A liposome may be classified as a unilamellar vesicle or a multivesicular vesicle.

The liposome may be a stimulus-sensitive liposome (i.e., sensitive to one or more stimuli), and the stimulus-sensitive liposome may control release of materials that are encapsulated therein. As used herein, "sensitive" to stimuli refers to the ability of a liposome to release its contents in response to exposure to one or more stimuli or the like, or to disintegrate in response to one or more stimuli or the like. Examples of the stimulus-sensitive liposome include a temperature-sensitive liposome, a pH-sensitive liposome, a chemical-sensitive liposome, a radiation-sensitive liposome, an ultrasound-sensitive liposome, or any combination thereof. The temperature-sensitive liposome, the pH-sensitive liposome, the chemical-sensitive liposome, the radiation-sensitive liposome, and the ultrasound-sensitive liposome may release materials that are contained therein at a certain temperature or temperature range, a certain pH or pH range, the presence of chemical substance, radiation conditions, and/or ultrasound conditions. The temperature may be, for example, in a range of about 25° C. to about 70° C., about 25° C. to about 65° C., about 25° C. to about 60° C., about 25° C. to about 55° C., about 25° C. to about 50° C., about 30° C. to about 50° C., about 35° C. to about 50° C., or about 37° C. (body temperature) to about 50° C. The pH may be greater than, equal to, or less than about 5.5, which is the pH of saline solution. The chemical substance may be a substance that makes tumor cells become more sensitive to effects of chemotherapy. Examples of the chemical substance include cyclosporine A, verapamil, biricodar, or any combination thereof. The irradiation may include alpha (α) rays, beta (β) rays, gamma (γ) rays, X-rays, or any combination thereof. As used herein "ultrasound" refers to a wave with a frequency greater than an audio frequency ranging from about 16 Hz to about 20 kHz. The ultrasound may be high intensity focused ultrasound (HIFU), and HIFU involves high-intensity ultrasound energies in one place to create a concentrated focus.

The term "hydrophobic" as used herein refers to properties of a material that does not allow it to easily combine with a water molecule or does not allow it easily dissolve in water, or refers to non-polar properties of the material. The term "hydrophobic" as used herein may be used interchangeably with the term "lipophilic". Hydrophobic materials may be classified according to water solubility thereof. For example, hydrophobic materials are slightly water soluble in a range of about 1 mg/ml to about 10 mg/ml, very slightly soluble in a range of about 0.1 mg/ml to about 1 mg/ml, and substantially insoluble at the level of about 0.1 mg/ml or less.

The term "active ingredient" as used herein refers to a biologically active substance, and examples thereof include a compound, a protein, a peptide, a nucleic acid, a nanoparticle, anticancer drugs, anti-angiogenesis inhibitors, anti-inflammatory drugs, analgesics, antiarthritics, sedatives, antidepressants, antipsychotics, tranquilizers, antianxiety drugs, narcotic antagonists, anti-Parkinson's disease drugs, cholinergic agents, immunosuppressive agents, antiviral agents, antibiotics, appetite suppressants, anticholinergics, antihistamines, anti-migraine drugs, hormones, vasodilators, birth control pills, antithrombotic agents, diuretics, antihypertensives, cardiovascular drugs, wrinkle-diminishing agent, inhibitors of skin aging, skin whitening agent, or any combination thereof.

The hydrophobic active ingredient may be a hydrophobic drug, imaging agent, or any combination thereof. The hydrophobic active ingredient includes a chemical substance (e.g., small molecule drug, imaging agent, etc.) or bio-drug (e.g., large molecule drug, such as a nucleic acid or polypeptide based drug) of which water solubility is 10 mg/ml or less. The hydrophobic active ingredient may be an anthracycline-based substance, hydrophobic glucocorticoid, a steroid-based substance, a taxane-based substance, a cyclic peptide-based substance, sorafenib, paclitaxel, docetaxel, doxorubicin, cyclosporine A, amphothericin B, indinavir, rapamycin, doxorubicin, coenzyme Q 10, ursodeoxycholic acid, ilaprazole, imatinib mesilate, tanespimycin, or any combination thereof. The anthracycline-based substance may be doxorubicin, daunorubicin, epirubicin, idarubicin, valrubicin, mitoxantrone, or any combination thereof. The hydrophobic glucocorticoid may be dexamethasone, trimacinolone, beclomethasone diproprionate, trimacinolone acetonide, trimacinolone diacetate, testosterone, budesonide, 17α-ethinylestradiol, levonorgestrel, fluticasone proprionate, or any combination thereof.

The term "imaging agent (i.e., a contrast medium)" as used herein refers to a substance used to enhance the contrast of an image showing tissues or blood vessels at the time of examination by a technique such as magnetic resonance imaging (MRI) and computed tomography (CT), by artificially increasing X-ray absorption differences of each tissue. The imaging agent may be classified as a positive imaging agent or a negative imaging agent. The imaging agent may include transition elements or chelate complexes of transition elements.

The polypeptide may be a polypeptide that binds with a hydrophobic active ingredient. The polypeptide may be, for example, albumin, transferrin, apolipoprotein, a fragment thereof, or any combination thereof. The albumin may be serum albumin, and the serum albumin may be human serum albumin (HSA) or bovine serum albumin (BSA). The transferrin is an iron-binding glycoprotein. The apolipoprotein may be apolipoprotein A, apolipoprotein B, apolipoprotein C, apolipoprotein D, apolipoprotein E, or apolipoprotein H.

The term "lipid bilayer" as used herein refers to a membrane made of two layers of lipid molecules. The lipid bilayer may have a similar thickness as that of a naturally existing bilayer, such as a cell membrane, a nuclear membrane, and a virus envelope. For example, the lipid bilayer may have a thickness of about 10 nm or less, for example, in a range of about 1 nm to about 9 nm, about 2 nm to about 8 nm, about 2 nm to about 6 nm, about 2 nm to about 4 nm, or about 2.5 nm to about 3.5 nm. The lipid bilayer is a barrier that keeps ions, proteins, and other molecules in an area, and/or prevents them from diffusing into other areas. The "lipid molecules" forming the lipid bilayer may be a molecule including a hydrophilic head and hydrophobic tails. The lipid molecule may have 14 to 50 carbon atoms.

The lipid bilayer may be phospholipid, a lipid conjugated to polyethylene glycol (PEG), cholesterol, elastin-like polypeptide, or any combination thereof.

As used herein "phospholipid" refers to a compound lipid containing phosphate ester within a molecule, and is a main component of biological membranes, such as cell membranes, endoplasmic reticulum, mitochondria, and myelin sheath around nerve fibers. The phospholipid includes a hydrophilic head and two hydrophobic tails. When the phospholipids are exposed to water, they arrange themselves into a two-layered sheet (a bilayer) with all of their tails pointing toward the center of the sheet. The center of this bilayer contains almost no water and also excludes molecules such as sugars or salts that dissolve in water but not in oil. The phospholipid may include phosphatidic acid, phosphatidylethanolamine, phosphatidylcholine, phosphatidylserine, phosphatidylinositol, phosphosphingolipid, or any combination thereof. Phosphatidylcholine (PC) may include choline as a head group and glycerophosphoric acid as a tail, wherein glycerophosphoric acid may be saturated fatty acid or unsaturated fatty acid and have 14 to 50 carbon atoms. Examples of the PC include 1,2-dipalmitoyl-sn-glycero-3-phosphocholine (DPPC), 1,2-distearoyl-sn-glycero-3-phosphocholine (DSPC), egg PC, soy bean PC, and any combination thereof.

In some embodiments, the lipid may be conjugated to poly(ethylene glycol) (PEG). The PEG-lipid conjugate may be, for example, PEGylated phosphatidylethanolamine (PE)-PEG. The PE may be saturated fatty acid, unsaturated fatty acid, mixed acyl chain, lysophosphatidylethanolamine, or any combination thereof. The lipid conjugated to PEG may, be for example, 1,2-distearoylphosphatidylethanolamine-methyl-polyethylene glycol (DSPE-PEG).

The term "cholesterol" as used herein refers any steroid compounds. Cholesterol also includes a cholesterol derivative, and examples thereof include sitosterol, ergosterol, stigmasterol, 4,22-stigmastadiene-3-on, stigmasterol acetate, lanosterol, cycloartenol, or any combination thereof. Cholesterol may enhance fluidity of a lipid bilayer and lower the permeability of the lipid bilayer.

The term "elastin-like polypeptide (ELP)" as used herein refers to one type of an amino acid polymer which undergoes conformation changes according to temperature. In some embodiments, ELP may be a polymer having "inverse phase transitioning behavior". The term "inverse phase transitioning behavior" as used herein refers to a substance having solubility in an aqueous solution at temperature below an "inverse phase transition temperature ($T_t$)" or a substance having insolubility in an aqueous solution at temperature above $T_t$. As the temperature rises, the ELP may transition into a tightly folded aggregate having solubility that is significantly decreased from the highly soluble elongated chain. That is, such an inverse phase transition may be induced by ELP further including a β-turn or distorted β-structure depending on the temperature. The ELP may have, for example, a phase transition temperature in a range of about 10° C. to about 70° C., about 20° C. to about 70° C., about 30° C. to about 70° C., about 37° C. (body temperature) to about 70° C., about 39° C. to about 70° C., about 40° C. to about 70° C., about 50° C. to about 70° C., or about 50° C. to about 70° C.

The complex containing the hydrophobic active ingredient and the polypeptide may be positioned in an interior space of the liposome. Here, the interior space of the liposome may be a liposome interior with respect to the structure of the lipid bilayer.

The liposome may have, for example, a diameter in a range of about 50 nm to about 500 nm, about 50 nm to about 400 nm, about 50 nm to about 300 nm, about 50 nm to about 200 nm, about 100 nm to about 200 nm, about 120 nm to about 200 nm, about 140 nm to about 200 nm, or about 140 nm to about 180 nm.

The liposome may include the polypeptide and the hydrophobic active ingredient in a concentration ratio in a range of about 1:01 to about 1:2. For example, the concentration ratio is about 1:0.1, about 1:0.2, about 1:0.3, about 1:0.4, about 1:0.5, about 1:0.6, about 1:0.7, about 1:0.8, about 1:0.9, about 1:1.0, about 1:1.1, about 1:1.2, about 1:1.3, about 1:1.4, about 1:1.5, about 1:1.6, about 1:1.7, about 1:1.8, about 1:1.9, or about 1:2.0.

In the liposome, the concentration of the polypeptide may be, for example, in a range of about 1 mg/ml to about 100 mg/ml, about 1 mg/ml to about 90 mg/ml, about 1 mg/ml to about 80 mg/ml, about 1 mg/ml to about 70 mg/ml, about 1 mg/ml to about 60 mg/ml, about 5 mg/ml to about 60 mg/ml, about 10 mg/ml to about 60 mg/ml, about 10 mg/ml to about 55 mg/ml, about 10 mg/ml to about 50 mg/ml, about 10 mg/ml to about 45 mg/ml, about 10 mg/ml to about 40 mg/ml, about 10 mg/ml to about 35 mg/ml, about 10 mg/ml to about 30 mg/ml, about 10 mg/ml to about 25 mg/ml, or about 10 mg/ml to about 20 mg/ml.

The liposomes of the present invention may exhibit a particular encapsulation efficiency of the polypeptide. As used herein, "encapsulation efficiency" refers to the amount of a substance retained in produced liposomes divided by the initial amount of the substance added for preparation of liposomes. The encapsulation efficiency may be, for example, in a range of about 0.1% to about 30%, about 0.1% to about 25%, about 0.1% to about 20%, about 0.1% to about 15%, about 0.1% to about 10%, about 0.1% to about 5%, about 0.5% to about 4.5%, about 1.0% to about 4.0%, about 1.0% to about 3.5%, about 1.0% to about 3.0%, about 1.2% to about 2.8%, about 1.4% to about 2.6%, about 1.6% to about 2.6%, about 1.8% to about 2.6%, about 2.0% to about 2.6%, or about 2.2% to about 2.6%.

According to another aspect of the present invention, provided is a pharmaceutical composition for delivering a hydrophobic active ingredient to a subject comprising a liposome, wherein the liposome comprises a complex comprising a hydrophobic active ingredient and a polypeptide; and a lipid bilayer, wherein the complex is contained in an interior space of the liposome.

The term hydrophobic, the active ingredient, the hydrophobic active ingredient, the polypeptide, the lipid bilayer, the interior space, and the liposome are the same as described, above.

The pharmaceutical composition may further include a pharmaceutically acceptable carrier or a diluent. The pharmaceutically acceptable carrier or diluent may be well known in the art. Examples of the pharmaceutically acceptable carrier or diluents include lactose, dextrose, sucrose, sorbitol, mannitol, starch, acacia gum, calcium phosphate, alginate, gelatin, calcium silicate, microcrystalline cellulose, polyvinylpyrrolidone, cellulose, water (for example, saline or sterile water), syrup, methyl cellulose, methylhydroxybenzoate, propylhydroxybenzoate, talc, magnesium stearate, mineral oil, Ringer's solution, buffer, maltodextrin solution, glycerol, ethanol, or any combination thereof. The pharmaceutical composition may further include a lubricant, a wetting agent, a sweetening agent, a flavoring agent, an emulsifier, a suspending agent, a preserving agent, or any combination thereof.

According to methods that are well known in the art, the pharmaceutical composition may be formulated and prepared in the form of a unit dose using the pharmaceutically acceptable carrier and/or diluents, or may be introduced and prepared in a multi-dose container. The pharmaceutical composition may be formulated in types of a solution of oil or aqueous medium, suspension, syrup, or emulsion. In some aspects, the pharmaceutical composition may be formulated in types of extracts, powders, powdered drugs, granules, tablets, or capsules. The pharmaceutical composition may further include dispersants or stabilizers. The aqueous medium may contain physiological saline or PBS.

According to another aspect of the present invention, provided is a method of delivering a hydrophobic active ingredient to a target site in the body of a subject comprising administering a liposome to a subject, wherein the liposome comprises a complex containing a hydrophobic active ingredient and a polypeptide; and a lipid bilayer, wherein the complex is contained in an interior space of the liposome; and applying a stimulus to the target site of the subject to release the complex containing the hydrophobic active ingredient and the polypeptide from the liposome.

The term hydrophobic, the active ingredient, the hydrophobic active ingredient, the polypeptide, the lipid bilayer, the interior space, and the liposome are the same as described, above.

The subject may be a mammal (e.g., humans).

The administration may be oral administration or parenteral administration. The parenteral administration may be, for example, intravenous, intradermal, intramuscular, intracavity (abdominal cavity, joints, or eye) or direct injection. The direct injection may involve injecting directly into a diseased site such as a tumor site. The liposome may be administered intravenously and accordingly brought to the target site such as a tumor site by blood flow. The suitable dosage of the liposome may be prescribed according to various factors such as formulation methods, administration methods, patient's age, weight, gender, and morbidity, foods, administration times, administration routes, excretion rates, and reaction sensitivity. Dosage of the liposome may be in a range of about 0.001 mg/kg to about 100 mg/kg.

The stimulus may be heat, pH variation, drug administration, irradiation, ultrasound, or any combination thereof. The heating may raise a temperature to a range of about 25° C. to about 70° C., about 25° C. to about 65° C., about 25° C. to about 60° C., about 25° C. to about 55° C., about 25° C. to about 50° C., about 30° C. to about 50° C., about 35° C. to about 50° C., or about 37° C. (body temperature) to about 50° C. The heating may be performed for about 1 second to about 48 hours, about 1 min to about 36 hours, about 5 min to about 24 hours, about 10 min to about 24 hours, about 30 min to about 12 hours, or about 1 hour to about 6 hours. The pH may be greater than, equal to or less than about 5.5, which is the pH of saline solution. The irradiation and ultrasound are as described above. The complex containing the hydrophobic active ingredient and the polypeptide may be released from the liposome by the stimulus.

The method may further include applying a second stimulus comprising ultrasound, a radio wave, a microwave, infrared, or any combination thereof to the target site of the subject. When the permeability of the cell membrane or blood vessels is increased, the absorption of the hydrophobic active ingredients may be increased. The ultrasound may be high-intensity focused ultrasound (HIFU). HIFU may have a frequency, for example, in a range of about 20 kHz to about 2.0 MHz, about 60 kHz to about 2.0 MHz, about 100 kHz to about 2.0 MHz, about 200 kHz to about 2.0 MHz, about 300 kHz to about 2.0 MHz, about 400 kHz to about 2.0 MHz, about 500 kHz to about 2.0 MHz, about 600 kHz to about 2.0 MHz, about 700 kHz to about 2.0 MHz, about 800 kHz to about 2.0 MHz, about 900 kHz to about 2.0 MHz, about 1.0 MHz to about 2.0 MHz, about 1.2 MHz to about 1.8 MHz, or about 1.4 MHz to about 1.6 MHz.

The method may further include preventing and treating disease by releasing the complex containing the hydrophobic active ingredient and the polypeptide from the liposome.

The term "prevention" as used herein refers to the inhibition of disease occurrence. The term "treatment" as used herein refers to the suppression, reduction, or elimination of disease development. Examples of diseases which may be prevented and treated include cerebrospinal tumor, head and neck cancer, lung cancer, breast cancer, thymoma, mesothelioma, esophageal cancer, stomach cancer, colon cancer, liver cancer, pancreatic cancer, bile duct cancer, kidney cancer, bladder cancer, prostate cancer, testicular cancer, germ cell tumor, ovarian cancer, uterine cervical cancer, endometrial cancer, lymphoma, acute leukemia, chronic leukemia, multiple myeloma, sarcoma, malignant melanoma, skin cancer, or any combination thereof. The released complex containing the hydrophobic active ingredient and the polypeptide may be absorbed into cells in the target site, and accordingly the polypeptide may be degraded by intracellular enzymes. When the polypeptide is degraded, the hydrophobic active ingredient may be released and thus, may exhibit its activity.

Hereinafter, one or more embodiments of the present invention will now be described more fully with reference to the following examples. However, these examples are provided only for illustrative purposes and are not intended to limit the scope of the present invention.

EXAMPLE 1

Preparation of a Complex Containing Sorafenib and Albumin and Measurement of Concentration of Sorafenib in the Complex Hydroxypropyl beta cyclodextrin (HPβCD) (Sigma Aldrich) was dissolved in distilled water to prepare a HPβCD solution in concentration of 185 mM. Next, sorafenib (SRF) (Santa Cruz Biotechnology, Inc.) was dissolved therein to prepare a mixed solution (a SRF/CD solution) containing 1.87 mM of SRF and 185 mM of HP+CD. Next, 1 ml of the SRF/CD solution was added to each of 3.3 mg, 6.7 mg, and 12.7 mg of Bovine Serum Albumin (BSA) (Sigma Aldrich), thereby preparing a mixed solution (a BSA/SRF/CD solution) containing BSA in concentration of each of 50 μM, 100 μM, and 190 μM.

The BSA/SRF/CD solution was put into a centrifugal filter (having 50 KDa molecular weight cut-off), and then centrifuged at a temperature of 4° C. for 10 minutes at a speed of 16000×g so as to remove the remaining SRF and CD that were not bound to BSA.

In order to confirm the concentration of SRF in the purified BSA/SRF/CD solution, acetonitrile (FISHER) was added to the BSA/SRF/CD solution so as to prepare a reactant containing supernatant and acetonitrile in a volume ratio of 3:7. The reactant was incubated at a temperature of 25° C. for 3 minutes to dissociate SRF from the BSA/SRF/CD solution, followed by being centrifuged at a temperature of 4° C. for 10 minutes at a speed of 13000×g. The pellets are removed so as to remove BSA from the BSA/SRF/CD solution. Then, BSA was removed from the pellets. Next, the supernatant was subject to high performance liquid chromatography (HPLC) (HPLC: Waters e2695, Column: Shiseido C18 CAPCELL PAK 4.6 mml.D.×250 mm) to quantify SRF. The concentration of SRF in the SRF/BSA solution was calculated, and the results were shown in FIG. 2 (y-axis: concentration of SRF (in μM) in the SRF/BSA solution, x-axis: concentration of BSA (in μM) in the SRF/BSA solution).

Figure 2:
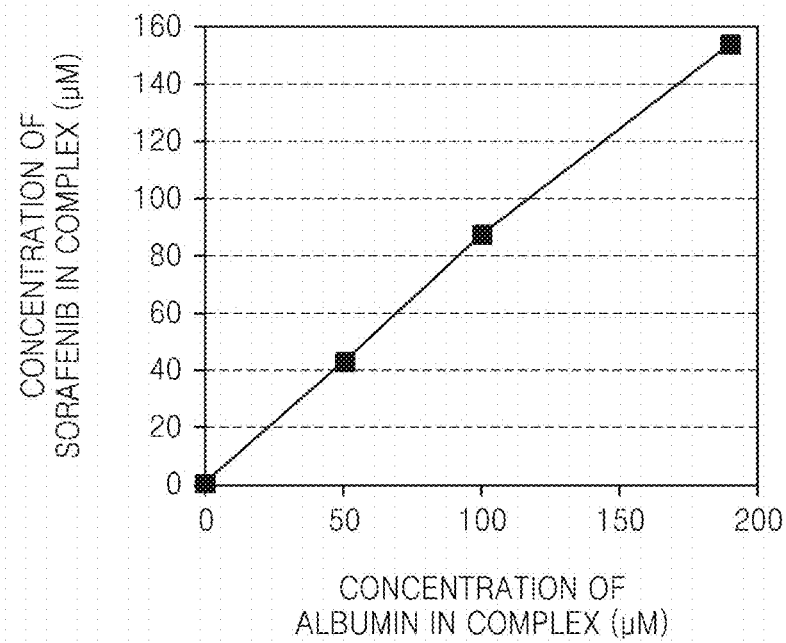
FIG. 2 is a graph showing concentrations of albumin and sorafenib in liposomes prepared according to an embodiment of the present invention.

As shown in FIG. 2, the concentration of SRF was increased in proportion to that of BSA in the SRF/BSA solution. As shown in FIG. 2, it was confirmed that the solution containing BSA and SRF in a concentration ratio of about 1:0.9 was obtained.

EXAMPLE 2

Preparation of Liposomes Including a Complex Containing SRF and Albumin, and Confirmation of Size of the Liposomes A solution containing SRF and albumin was prepared by adding phosphate buffered saline (PBS) to the solution containing SRF and albumin prepared in the same manner as in Example 1, wherein the concentration of SRF was 60 mg/ml with respect to albumin contained in the complex solution.

Liposomes were prepared in the form of unilamellar vesicle by mixing 1,2-dipalmitoyl-sn-glycero-3-phosphocholine (DPPC), 1,2-d istearoyl-sn-glycero-3-phosphoethanolamine-N-[methoxy(polyethylene glycol)-2000] (ammonium salt) (DSPE-PEG), cholesterol, and elastin-like polypeptide in a molar ratio of 55:2:4:1.1.

In detail, SA-V3-NH$_2$ (Peptron, Inc.) was dissolved in an ethanol solution, and DPPC (Avanti Polar lipids, Inc.), DSPE-PEG (Avanti Polar lipids, Inc.), cholesterol (Avanti Polar lipids, Inc.), and SRF (Bayer) were dissolved in a chloroform solution. The ethanol solution and the chloroform solution were mixed in a round bottom flask, and the solvent was evaporated at room temperature using a rotary evaporator so as to form a lipid thin film on the inner wall of the round bottom flask.

1 ml of the SRF/albumin complex solution was added to the round bottom flask at room temperature so as to hydrate the lipid thin film. The hydrated resulting solution was then subject to vortexing and sonication treatment. The resulting solution was extruded by AVANTI® Mini-Extruder (Avanti Polar Lipids, Inc.) using polycarbonate films (Waters Corp.) with a pore size of 400 nm, 200 nm, or 100 nm in diameter, thereby preparing liposomes in the form of unilamellar vesicles. The solvent of the prepared liposome solution was replaced with PBS by flowing PBS through a PD-10 desalting column (GE Healthcare).

Figure 3:
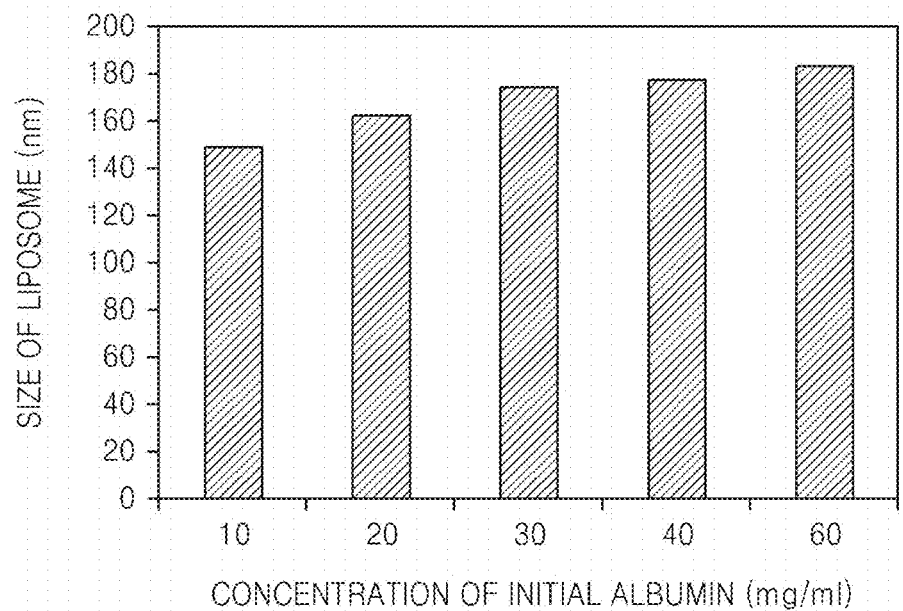
FIG. 3 is a graph showing the size of liposomes at various concentrations of albumin in liposomes prepared according to an embodiment of the present invention.

A dynamic light scattering (DLS) analyzer (Malvern Instruments Ltd) was used to measure the size of the prepared liposomes, and the measured size of the liposomes with respect to the concentration of initial albumin was shown in FIG. 3. In spite of the increased concentration of the initial albumin, nanoparticles having relatively uniform size were formed in which a difference of the size was in a range of about 20 nm to about 30 nm in diameter. As shown in FIG. 3, the prepared liposomes had a diameter in a range of about 140 nm to about 180 nm, and had an average diameter of about 170 nm.

EXAMPLE 3

Confirmation of Shape of Liposomes Including a Complex Containing SRF and Albumin Liposomes were prepared in the same manner as in Example 1 using an albumin solution containing initial albumin in concentration of 30 mg/ml or 100 mg/ml. The shape of the prepared liposomes was confirmed by a transmission electron microscope (TEM).

Figure 4A:
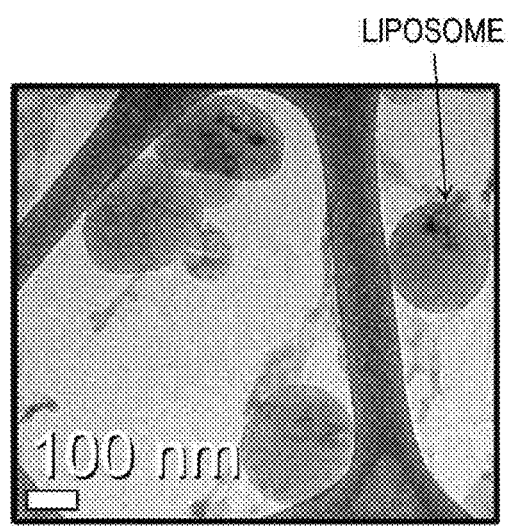
FIG. 4A is a transmission electron microscope (TEM) image of liposomes prepared using a low concentration albumin solution according to an embodiment of the present invention.
Figure 4B:
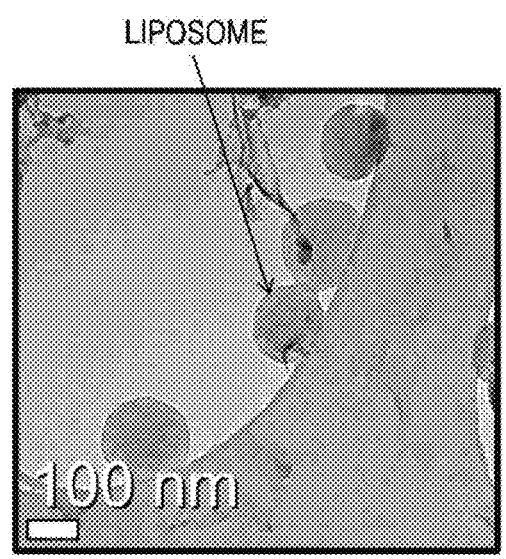
FIG. 4B is a TEM image showing liposomes prepared using a high concentration albumin solution according to another embodiment of the present invention.

In detail, the prepared liposomes were observed after they were loaded into holey carbon film-supported grids. The grids were then dipped in liquid nitrogen and transferred to a cyotransfer holder (Gatan). Images were obtained using a Tecnai F20 field emission gun electronic microscope equipped with a CCD camera (2k, Gatan) that operates at 200 kV (FEI). The obtained images were shown in FIGS. 4A and 4B. FIG. 4A is a TEM image showing the liposomes prepared using the albumin solution containing the initial albumin in a low concentration of 30 mg/ml. FIG. 4B is a TEM image showing the liposomes prepared using the albumin solution containing the initial albumin in a high concentration of 100 mg/ml.

As shown in FIGS. 4A and 4B, spherical liposomes having a diameter in a range of about 100 nm to about 200 nm were observed. It was also confirmed that the liposomes prepared by using the albumin solution containing the initial albumin in high concentration had a thicker lipid bilayer than the liposomes prepared by using the albumin solution containing the initial albumin in low concentration.

EXAMPLE 4

Confirmation of Encapsulation Efficiency and Release Efficiency of Albumin in Liposomes Liposomes were prepared in the same manner as in Example 1, except that HSA (Abcam) conjugated to fluorescein isothiocyanate (Abcam) was used and SRF was excluded.

In the preparation of liposomes, albumin at a variety of concentrations of 10 mg/ml, 20 mg/ml, 30 mg/ml, 40 mg/ml, and 60 mg/ml was encapsulated in liposomes, and albumin that was not encapsulated in the liposomes was removed by using a Sepharose CL-B2 column. The purified liposomes were irradiated by an absorption/emission wavelength of 460 nm/540 nm so as to measure the fluorescence. Then, the encapsulation efficiency of albumin was calculated according to the following formula, and the results were shown in Table 1 below.

Encapsulation efficiency (%)=amount of albumin retained in produced liposomes/amount of initial albumin added for preparation of liposomes×100

TABLE 1

| Concentration of initial albumin (mg/ml) | Encapsulation efficiency (%) |
|---|---|
| 60 | 1.6 |
| 40 | 1.4 |
| 30 | 1.8 |
| 20 | 2.4 |
| 10 | 2.6 |

Next, the prepared liposomes were incubated at a temperature of 50° C. for 20 minutes, followed by being centrifuged at a temperature of 4° C. for 10 minutes at a speed of 13000×g so as to obtain HSA conjugated to FITC (HSA-FITC). The fluorescence of the obtained HSA-FITC was measured so as to calculate the concentration of HSA released from the liposomes. The results were shown in FIG. 5.

Figure 5:
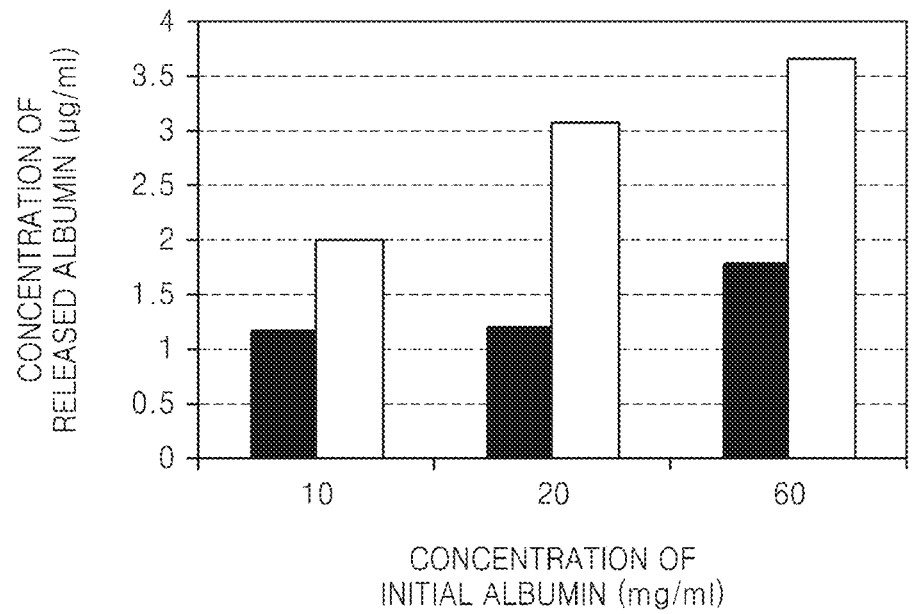
FIG. 5 is a graph showing concentrations of albumin released from liposomes before and after incubation at 50° C. for 10 minutes, according to an embodiment of the present invention (black bar: before performing incubation, white bar: after performing incubation)

As shown in FIG. 5, the amount of the released HSA after the incubation at a temperature of 50° C. was greater than that of the released HSA at a temperature of 25° C. Therefore, it was confirmed that the release of HSA from the liposomes may be controlled according to temperature.

EXAMPLE 5

Confirmation of Absorption of Albumin in Cells

Absorption efficiency of HSA (Abcam)-FITC in cells was confirmed.

In detail, HSA-FITC at a variety of concentrations of 1.25 mg/ml, 2.5 mg/ml, 5 mg/ml and 10 mg/ml was added to about 20,000 HepG2 liver carcinoma cells, followed by being incubated at a temperature of 37° C. for 48 hours. Next, the incubated cells were washed out with PBS. HSA absorbed in the cells was confirmed by a fluorescence microscope, and a graph showing average fluorescence intensity was shown in FIG. 6 (Normalization by Imaging Area, n=5, ANOVA and Tukey's test, mean±SEM, *: $P<0.05$, : $P<0.01$, *: $P<0.001$) (x-axis: concentration of HSA-FITC, y-axis: average fluorescence intensity of HSA-FITC).

Figure 6:
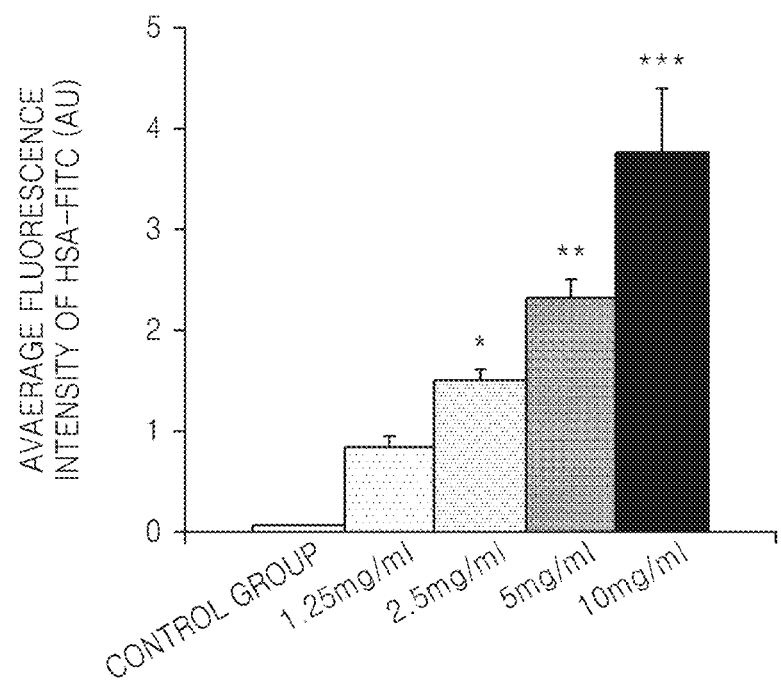
FIG. 6 is a graph showing average fluorescence intensity (artificial unit: AU) of albumin conjugated to fluorescein isothiocyanate (FITC) absorbed in cells depending on concentration of the albumin conjugated to FITC (x-axis) prepared according to an embodiment of the present invention.

As shown in FIG. 6, it was confirmed that HSA was efficiently absorbed in the cells as the concentration of HSA increased. That is, it is deemed that HSA may be used as a drug delivery carrier for the treatment of cancer cells.

EXAMPLE 6

Confirmation of Cytotoxicity of Complex Containing SRF and Albumin

The liposomes prepared in the same manner as in Example 1 were incubated with cells to confirm cell proliferation.

The liposomes prepared in the same manner as in Example 1 were added in different concentrations to about 5,000 HepG2 liver carcinoma cells, followed by being incubated at a temperature of 37° C. for 46 hours. The viability of the cultured cells was measured using a CCK-8 kit (Dojindo), and the results were shown in FIG. 7 (●: albumin, ■: complex containing SRF and albumin).

Figure 7:
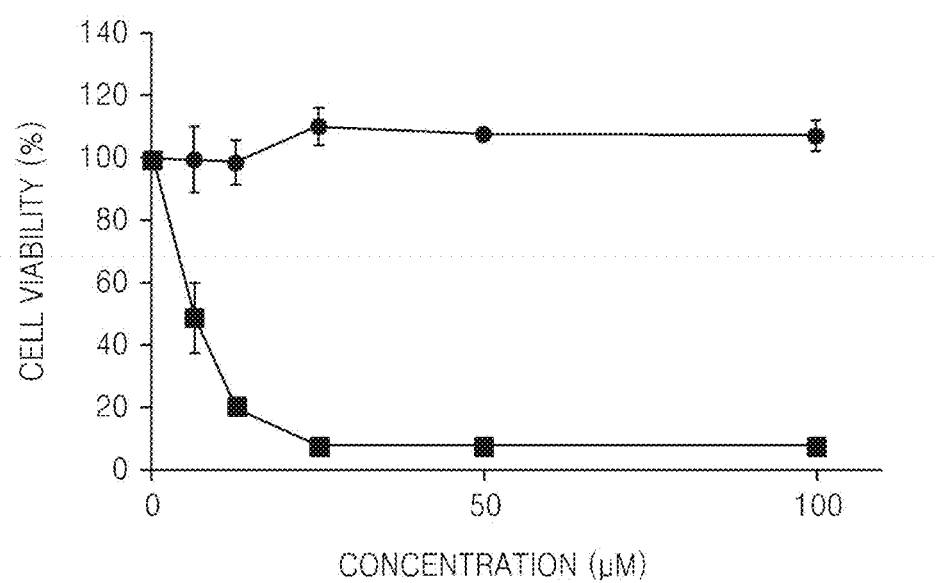
FIG. 7 is a graph showing viability of cells that are treated with a complex containing sorafenib and albumin prepared according to an embodiment of the present invention (●: albumin, ■: complex containing sorafenib and albumin).

As shown in FIG. 7, it was confirmed that albumin itself was not toxic and the half maximal inhibitory concentration ($IC_{50}$) of the complex containing SRF and albumin was about 6.25 μM while the $IC_{50}$ of SRF was about 5 μM. Therefore, it was confirmed that the complex containing SRF and albumin had a similar cytotoxicity value with that of SRF.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A liposome providing controlled release of a hydrophobic active ingredient, the liposome comprising:
   a lipid bilayer encapsulating a complex in the interior space of the liposome,
   wherein the complex comprises a hydrophobic active ingredient and a polypeptide,
   wherein the lipid bilayer comprises (i) an elastin-like polypeptide and (ii) a phospholipid, a lipid conjugated to polyethylene glycol, cholesterol, or any combination thereof,
   wherein the liposome is sensitive to temperature, pH, chemicals, radiation, ultrasound or any combination thereof,
   wherein the polypeptide comprises albumin, transferrin, apolipoprotein, a fragment thereof, or any combination thereof.

2. The liposome according to claim 1, wherein the hydrophobic active ingredient comprises a hydrophobic drug, an imaging agent, or any combination thereof.

3. The liposome according to claim 2, wherein the hydrophobic active ingredient comprises sorafenib, paclitaxel, docetaxel, doxorubicin, cyclosporine A, amphothericin B, indinavir, rapamycin, coenzyme Q10, ursodeoxycholic acid, ilaprazole, imatinib mesilate, tanespimycin, or any combination thereof.

4. The liposome according to claim 1, wherein the phospholipid comprises phosphatidic acid, phosphatidylethanolamine, phosphatidylcholine, phosphatidylserine, phosphatidylinositol, phosphosphingolipid, or any combination thereof.

5. The liposome according to claim 1, wherein the phospholipid comprises 1,2-dipalmitoyl-sn-glycero-3-phosphocholine (DPPC), 1,2-distearoyl-sn-glycero-3-phosphocholine (DSPC), egg phosphatidylcholine (PC), soy PC, or any combination thereof.

6. The liposome according to claim 1, wherein the polypeptide and the hydrophobic active ingredient are present in a concentration ratio of about 1:0.1 to about 1:2.

7. The liposome according to claim 1, wherein the weight of the polypeptide has a concentration of about 1 mg/ml to about 100 mg/ml with respect to the volume of the liposome.

8. The liposome according to claim 7, wherein the weight of the polypeptide has a concentration of about 10 mg/ml to about 30 mg/ml with respect to the volume of the liposome.

9. The liposome according to claim 1, wherein the ratio of the weight of the polypeptide to the weight of the liposome is in a range of about 0.1% to about 30% with respect to the liposome.

10. A pharmaceutical composition comprising:
a liposome providing controlled release of a hydrophobic active ingredient, the liposome comprising a lipid bilayer encapsulating a complex in the interior space of the liposome,
wherein the complex comprises a hydrophobic active ingredient and a polypeptide and a carrier,
wherein the lipid bilayer comprises (i) an elastin-like polypeptide and (ii) a phospholipid, a lipid conjugated to polyethylene glycol, cholesterol, or any combination thereof,
wherein the liposome is sensitive to temperature, pH, chemicals, radiation, ultrasound or any combination thereof,
wherein the polypeptide comprises albumin, transferrin, apolipoprotein, a fragment thereof, or any combination thereof.

11. A method of delivering an active ingredient to a target site in the body of a subject, the method comprising:
administering a pharmaceutical composition of claim 10 to a subject; and
applying a stimulus to a target site of the subject to release the complex containing the hydrophobic active ingredient and the polypeptide from the liposome.

12. The method according to claim 11, wherein the stimulus comprises heat, pH variation, drug administration, irradiation, ultrasound, or any combination thereof.

13. The method according to claim 12, wherein the stimulus is heat and the heat raises the temperature of the target site to a range of about 25° C. to about 70° C.

14. The method according to claim 12, wherein the heat is applied from about 1 second to about 48 hours.

15. The method according to claim 11, further comprising:
applying ultrasound, radio frequency, microwave, infrared ray, or any combination thereof to the target site of the subject.

16. The method according to claim 15, wherein the ultrasound is high intensity focused ultrasound (HIFU).

* * * * *